United States Patent
Streit et al.

(10) Patent No.: US 8,043,262 B2
(45) Date of Patent: Oct. 25, 2011

(54) INJECTION DEVICE WITH CONTROLLED NEEDLE RETRACTION

(75) Inventors: Ursina Streit, Bern (CH); Markus Bollenbach, Bern (CH); Patrick Hostettler, Hasle-Ruegsau (CH); Daniel Kuenzli, Langendorf (CH)

(73) Assignee: TecPharma Licensing AG, Burgdorf (CH)

( * ) Notice: Subject to any disclaimer, the term of this patent is extended or adjusted under 35 U.S.C. 154(b) by 63 days.

(21) Appl. No.: 12/563,789

(22) Filed: Sep. 21, 2009

(65) Prior Publication Data

US 2010/0137801 A1 Jun. 3, 2010

Related U.S. Application Data

(63) Continuation of application No. PCT/CH2008/000118, filed on Mar. 19, 2008.

(30) Foreign Application Priority Data

Mar. 22, 2007 (DE) .......................... 10 2007 013 836

(51) Int. Cl.
*A61M 5/20* (2006.01)
(52) U.S. Cl. ........................................ 604/137; 604/138
(58) Field of Classification Search .......... 604/192–198, 604/138, 187, 229, 156, 157, 137, 110
See application file for complete search history.

(56) References Cited

U.S. PATENT DOCUMENTS

| 4,194,505 | A | * | 3/1980 | Schmitz | 604/138 |
| 6,387,078 | B1 | | 5/2002 | Gillespie, III | |
| 6,569,124 | B1 | * | 5/2003 | Perouse | 604/198 |
| 2007/0260193 | A1 | * | 11/2007 | Chin et al. | 604/198 |

FOREIGN PATENT DOCUMENTS

| DE | 20 2007 000578 U1 | 3/2007 |
| EP | 0 516 473 A | 12/1992 |
| EP | 1 743 666 A | 1/2009 |
| FR | 2 774 294 A | 8/1999 |
| WO | WO 99/03529 A | 1/1999 |
| WO | WO 2004/024211 A | 3/2004 |
| WO | WO 2004/054645 A | 7/2004 |

* cited by examiner

*Primary Examiner* — Nicholas D Lucchesi
*Assistant Examiner* — Weng Lee
(74) *Attorney, Agent, or Firm* — Dorsey & Whitney LLP; David E. Bruhn, Esq.

(57) ABSTRACT

An injection device, in some embodiments an autoinjector, which includes a housing, an actuating sleeve carried by the device to be movable relative to the housing and which can be placed at a point of injection in a position of insertion, an injection needle extendable from the end of the injection device when the injection device is in the position of insertion and moveable into the interior of the injection device, and an actuating cam arranged in an axially fixed manner relative to the injection needle and engageable in a locking recess when the injection device is in the position of insertion to prevent the injection needle from being moved into the interior of the injection device, said actuation cam being releasable from engagement with the locking recess by the actuating sleeve, thereby releasing the injection needle for movement into the injection device.

19 Claims, 13 Drawing Sheets

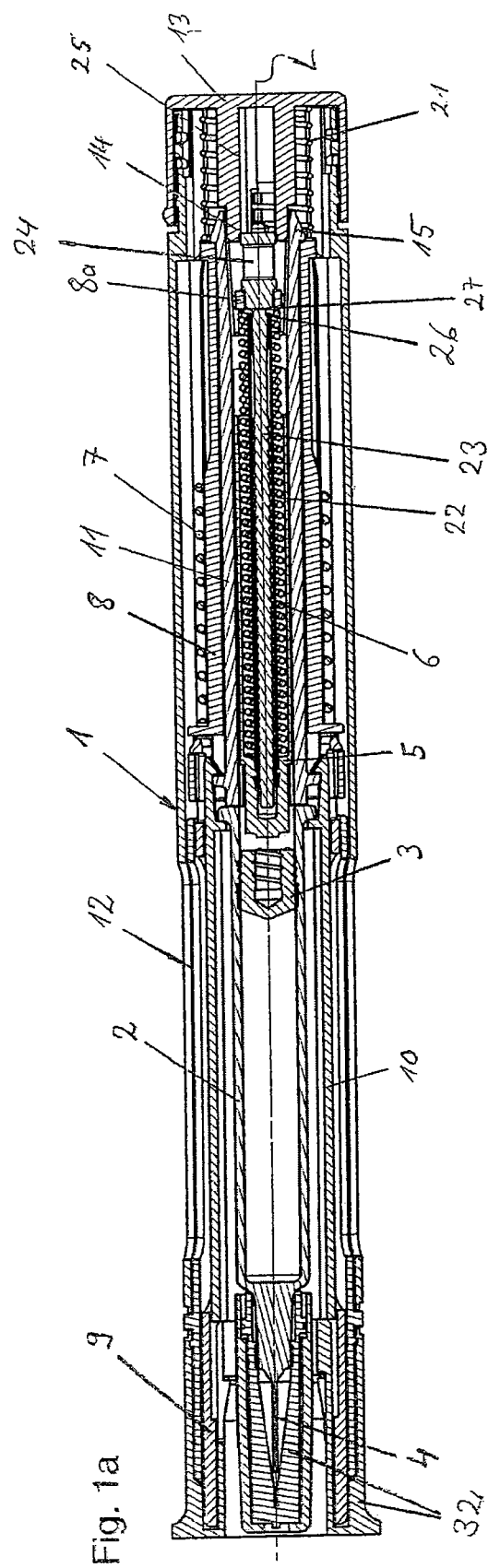
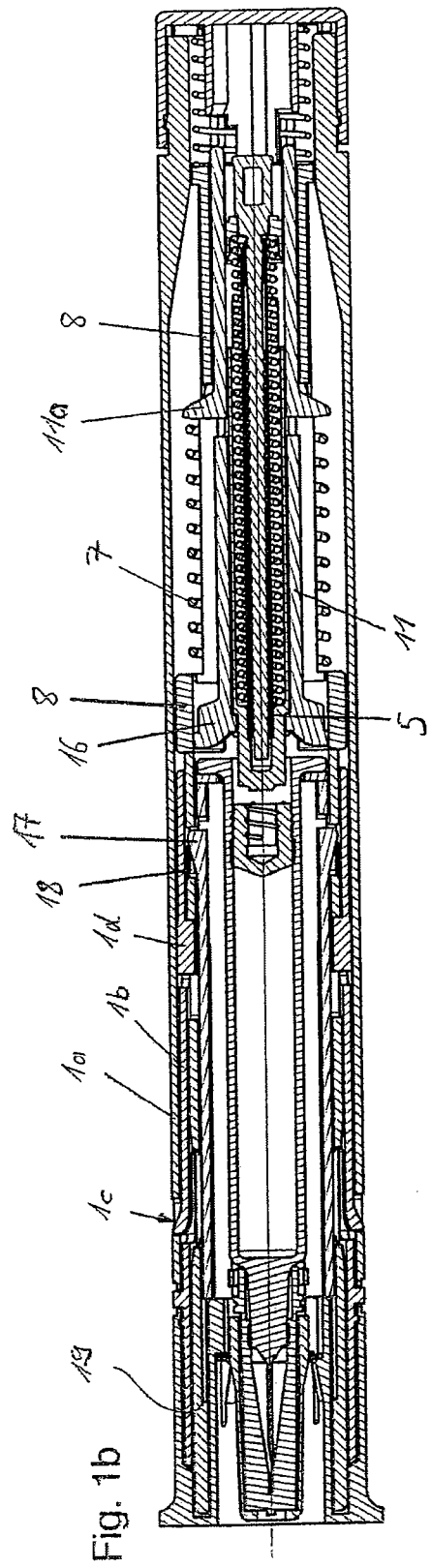

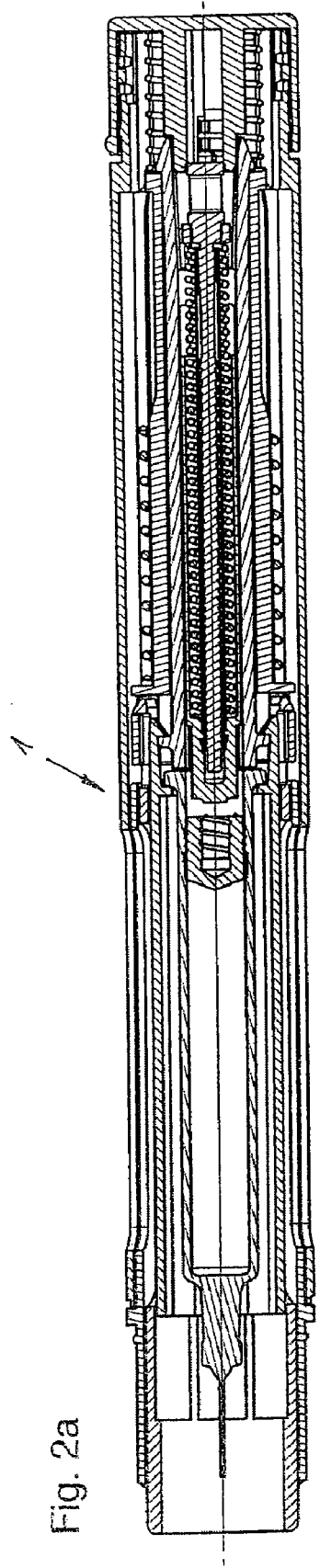
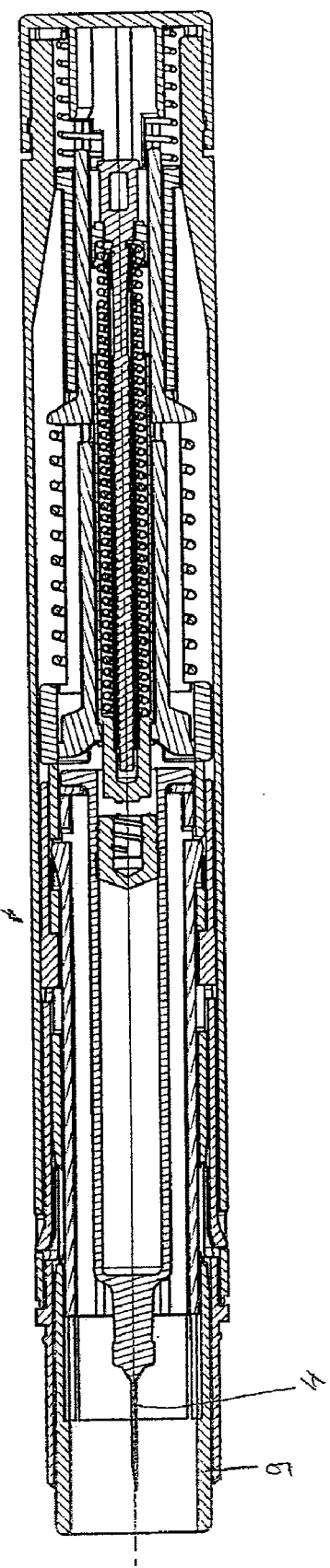
Fig. 2a
Fig. 2b

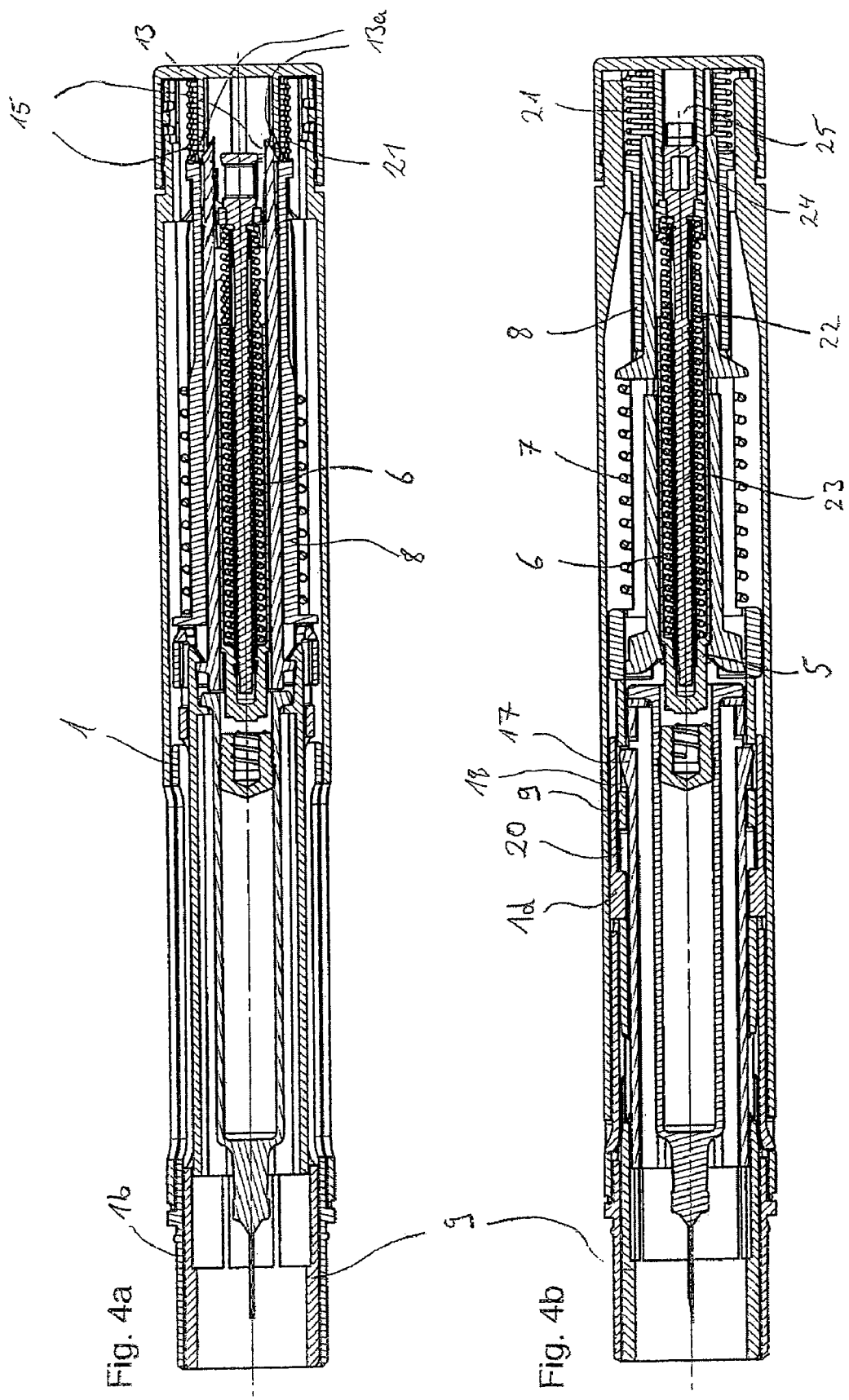

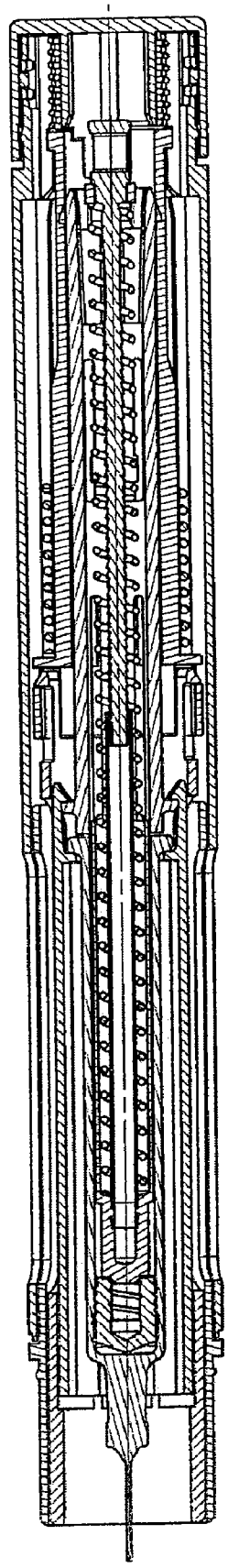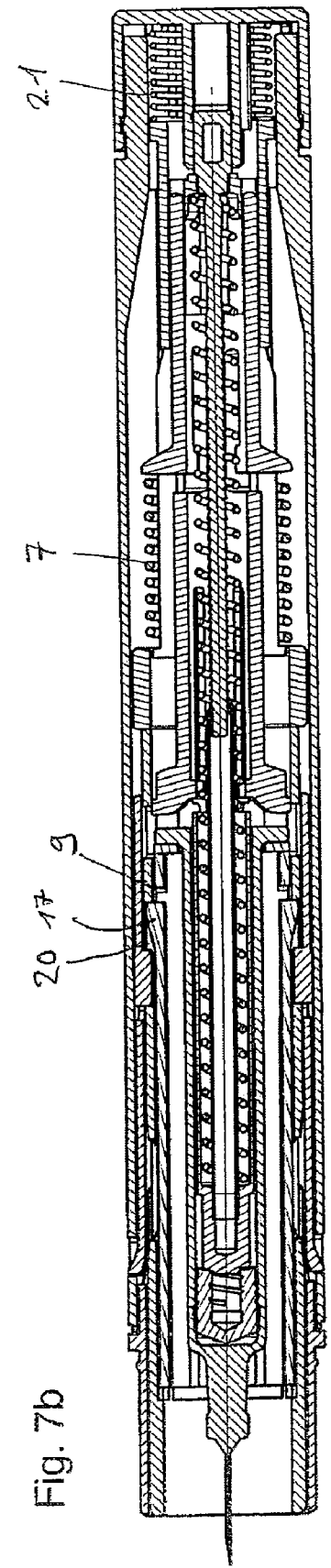

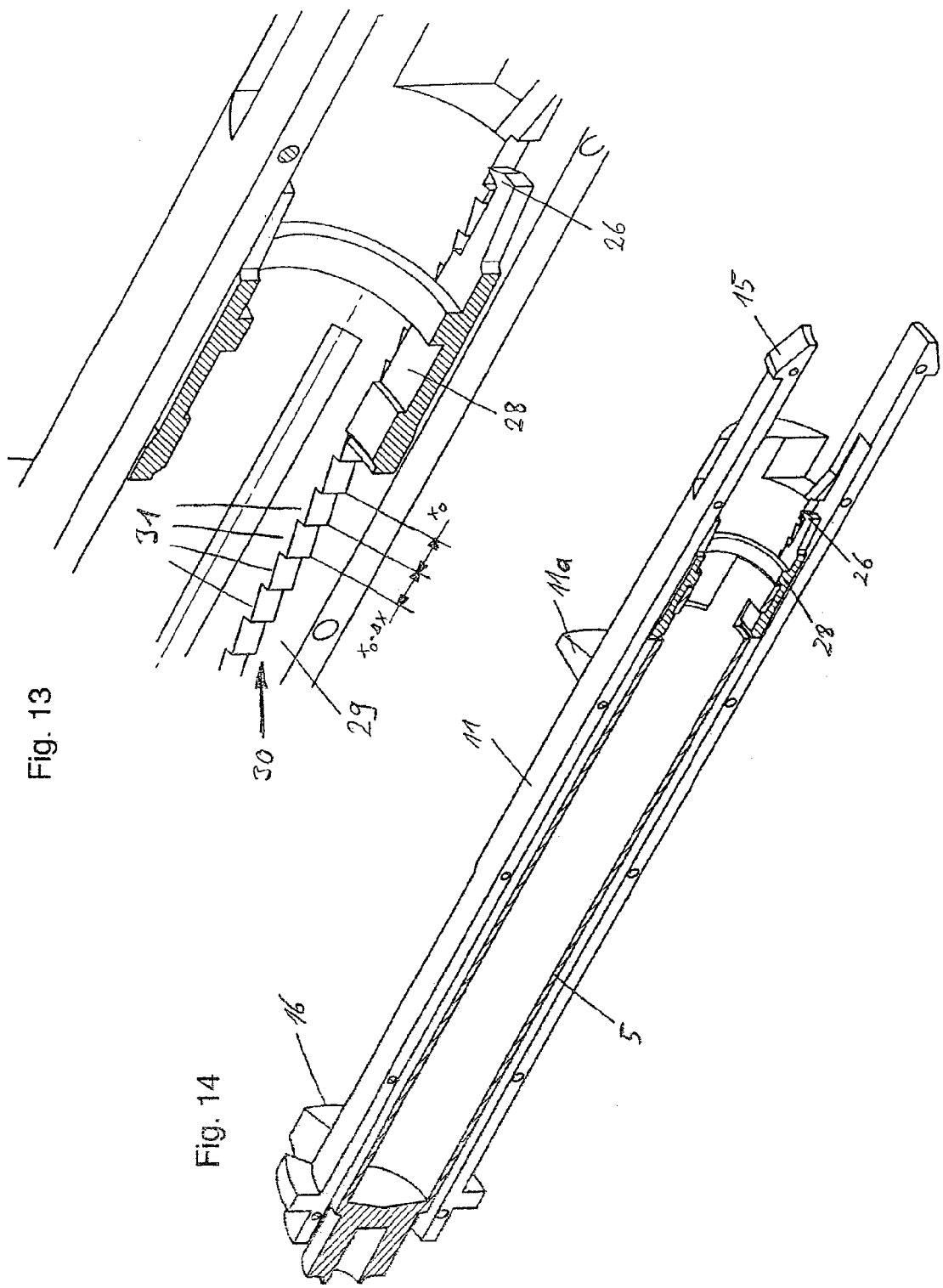

INJECTION DEVICE WITH CONTROLLED NEEDLE RETRACTION

CROSS-REFERENCED RELATED APPLICATIONS

This application is a continuation of International Patent Application PCT/CH2008/000118 filed Mar. 19, 2008, which claims priority to German Patent Application DE 10 2007 013 836.0 filed Mar. 22, 2007, the entire content of both of which is incorporated herein by reference.

BACKGROUND

The present invention relates to devices for injecting, administering, infusing, delivering or dispensing a substance, and to methods of making and using such devices. More particularly, it relates to injection devices for administering a liquid product such as a medicinal substance or a medicament and, more particularly, to an injection device and a method of moving or retracting a needle associated with the injection device from a piercing position in a controlled manner.

A known utilization or method of use of injection devices, including automatic injectors, is for a needle to be injected in a patient by a mechanism of the device, after which the product is administered to the patient through the needle. After the product has been successfully dispensed, the needle is covered and/or pulled back into the injection device.

For example, U.S. Pat. No. 6,387,078 discloses an injection device in which a needle firstly effects a piercing movement with the aid of a driving spring and the product is then dispensed by the urging of the driving spring. As the driving spring moves forward, a return spring is simultaneously tensed. Immediately on reaching the end position of a dispensing movement, the driving spring is uncoupled from the return spring so that the return spring immediately retracts or moves the needle back into the housing. As this happens, it may be that the medicament is not or has not been completely injected into the patient's tissue and a small amount is lost. This is annoying, especially in the case of expensive drugs. The amount that is lost can also lead to problems with respect to the actual dose administered.

SUMMARY

Accordingly, one object of the present invention is to provide an injection device, and a method of making and using the device, wherein a user of the device has an easy way of determining when the needle should be retracted.

In one embodiment, the present invention comprises an injection device, in some embodiments an autoinjector, which comprises a housing, an actuating sleeve carried by the injection device to be movable relative to the housing and which can be placed at a point of injection in a position of insertion, an injection needle extendable from the end of the injection device when the injection device is in the position of insertion and moveable into the interior of the injection device, and an actuating cam arranged in an axially fixed manner relative to the injection needle and engageable in a locking recess when the injection device is in the position of insertion to prevent the injection needle from being moved into the interior of the injection device, said actuation cam being releasable from engagement with the locking recess by the actuating sleeve, thereby releasing the injection needle for movement into the injection device.

An injection device in accordance with the present invention may be designed to dispense a product from a product container, for example. In some preferred embodiments, an injection device in accordance with the present invention may be of the type referred to as automatic injectors and may be provided with a mechanism which enables automatic piercing by the needle, followed by automatic dispensing of the product. Once the product has been dispensed, the needle automatically is and/or must be retracted into the automatic injector.

In one embodiment, the present invention comprises an injection device, e.g. autoinjector, which comprises a housing, an actuating sleeve which is mounted to be movable relative to the housing and which can be placed on a point of injection of a patient with the distal end of the injection device, an injection needle which protrudes over the distal end of the injection device when in the position of insertion and which can be moved back or retracted into the interior of the injection device, and an actuating cam which is arranged in an axially fixed manner relative to the injection needle and which engages in a locking recess when in the position of insertion to prevent the injection needle from being retracted into the interior of the injection device, said actuation cam being releasable from the engagement with the locking recess via the actuating sleeve, thereby releasing the injection needle for the retracting movement.

Generally, an injection device in accordance with the present invention has a housing. The housing has a distal (front or forward) end and a proximal (rear) end. The distal end is the end to which the needle is attached. The proximal end is the end lying opposite the distal end.

In some embodiments, the injection device has an operating sleeve which is mounted so that it is able to move relative to the housing. The operating sleeve and/or the distal end of the injections device can be placed at or on an injection site of a patient. In some preferred embodiments, the operating sleeve extends beyond the distal end of the housing by a short distance. This short distance should be dimensioned so that when the operating sleeve is moved in the proximal direction and back in the distal direction by this short distance, switching operations can be performed. For example, these might include triggering of a piercing movement in the case of a movement in the proximal direction and a retracting movement for the needle in the case of a movement back in the distal direction. In some embodiments, an elastic means such as a resilient element or spring may be provided, which can be tensed by the movement of the operating sleeve in the proximal direction and/or by which the operating sleeve can be driven to effect the movement in the distal direction. This being the case, the elastic means has a rebounding characteristic and may be described as a return spring, for example. In some embodiments, the elastic means is used to re-set the operating sleeve back in the initial position if it has not been moved back in the proximal direction far enough to trigger a switching operation and/or may co-operate during a switching operation caused by the movement of the operating sleeve in the distal direction.

In some preferred embodiments, the operating sleeve can be pushed out of its most distal position so far in the proximal direction that its distal end is more or less flush with the distal end of the housing, which corresponds to the state in which the user has placed the injection device on the injection site of the patient and pushed on it.

In some embodiments, the injection device has an associated injection needle, which extends out beyond the distal end of the injection device in a piercing position. The injection needle may be attached to a product container, for example, to the distal end of the container. The injection needle has at least one fluid connection to the interior of the product container.

The product to be administered, e.g. a liquid, is disposed in the interior of the product container. This product might be a hormone, such as growth hormone for example, or insulin for treating diabetes or some other medicament. The product container is closed at its proximal end by a plunger mounted or carried able to slide relative to the product container. When the plunger is moved in the direction toward the distal end of the product container, the product is dispensed through the needle. The needle may be connected to the product container in an axially fixed arrangement.

In some preferred embodiments of the present invention, the injection needle and the product container are disposed so that they are able to move along the longitudinal axis of the injection device relative to the housing. For example, the injection needle can be moved from an initial position in which it is disposed completely in the distal end of the injection device, i.e. not projecting beyond the distal end of the device, into the piercing position. In the piercing position, the needle extends beyond the distal end of the device by a distance which corresponds to the injection depth of the needle in the tissue of the patient. In some preferred embodiments, the injection needle can be pulled or moved back from the piercing position once the product has been dispensed, completely into the distal end of the injection device, i.e. into an end position of the injection needle. An advantage of this is that there can be no inadvertent piercing by the needle in the end position, but also in the initial position.

In some embodiments, the injection device has a switch cam, which is axially stationary with respect to the injection needle and locates or is received in a lock window when the needle is in the piercing position. A purpose of this locating action is to prevent the injection needle from moving back into the interior of the injection device. This is desirable if the product has not yet been fully dispensed. In some preferred embodiments, the switch cam is indirectly connected to the injection needle. For example, the switch cam may be disposed on a holder for the product container, or may be disposed on the product container. In some embodiments, the switch cam may be disposed on a part of the drive structure, which comprises at least the product container and the holder for the product container, for example. In some embodiments, the switch cam is resiliently disposed on a part of the drive structure. For example, the switch cam may be resiliently and integrally joined to the part of the drive structure via an elastic arm. However, this does not rule out resilient arrangements of other types.

In some preferred embodiments, the lock window is disposed radially outside of the switch cam. The switch cam may engage in the lock window by a movement directed radially outwardly. The lock window is bounded distally and proximally by two parts which are able to move relative to one another. The housing or an element secured to the housing bound the lock window distally and the operating sleeve bounds the lock window proximally.

In some preferred embodiments, the width of the lock window pointing in the longitudinal direction of the injection device can be varied, in which case the switch cam can be moved into engagement with the lock window or can be moved out of engagement with the lock window depending on the width of the lock window. In other words, the width of the lock window is dynamic. Consequently, the lock window can disappear altogether, for example, if its distal and proximal boundaries move into contact with one another.

In accordance with some embodiments of the present invention, the switch cam can be moved out of engagement with the lock window by the operating sleeve. As a result, the injection needle is released for the retracting movement out of the piercing position into the end position. Since the user of the device is able to control the position of the operating sleeve at will on the basis of the pressure by which the injection device is applied to the injection site, he or she can therefore determine the time at which the injection needle is retracted into the housing. To this end, the user merely reduces the contact pressure of the injection device on the injection site. This will cause the operating sleeve to move in the distal direction.

In some preferred embodiments, the operating sleeve is moved out of engagement with the lock window as the operating sleeve moves in the distal direction. The width of the lock window pointing in the longitudinal direction of the injection device is reduced and removed as a result of this movement so that the switch cam is moved out of engagement with the lock window.

An advantage of being able to selectively control the instant at which the needle is retracted at will is that a user of an injection device in accordance with the present invention can decide how long the needle should remain in the tissue after product dispensing to ensure that all the product is dispensed, e.g. on the basis of experience or depending on the viscosity of the liquid. An exemplary length of time is a period of 5 seconds, although this is given only as an example. The waiting time may vary and should ensure that the liquid product is better distributed in the tissue and the product is fully dispensed due to the inertia of the product dispensing process. This offers economic advantages on the one hand, and advantages in terms of ascertaining the actual product dose administered on the other hand.

In some preferred embodiments, at least two conditions should be satisfied before the needle is retracted, e.g. that product dispensing has finished and the operating sleeve has been moved in the distal direction.

In some preferred embodiments, the switch cam has a stop surface pointing in the proximal direction, which is able to co-operate with the operating sleeve so that the switch cam can also be driven by the operating sleeve as the operating sleeve moves in the distal direction when the switch cam is disposed in the lock window. In some preferred embodiments, a movement of the switch cam in the proximal direction is prevented when the stop surface of the switch cam is in abutment with the proximal boundary of the lock window. This prevents the needle and the entire drive structure from being pushed in the proximal direction.

In some embodiments, in the distal direction, the switch cam may be shaped so that it can be moved by the housing or an element secured to the housing out of engagement with the lock window or/and it can be moved by the operating sleeve out of engagement with a cut-out disposed in the operating sleeve. Such a shape might be an oblique surface pointing in the distal direction, for example, which moves the switch cam out of the lock window based on the principle of an inclined plane. In some preferred embodiments, the movement by which the switch cam is moved out of engagement with the lock window is a radial movement, e.g. a movement directed radially inwardly.

In some embodiments, when the device is in the initial position, the switch cam may be engaged in a cut-out disposed on or associated with the operating sleeve. This cut-out is disposed proximally with respect to the lock window. The cut-out is bounded both distally and proximally by the operating sleeve. The cut-out may be an aperture or a pocket. The switch cam can be moved out of engagement with the cut-out by a movement of the switch cam in the distal direction, such as occurs when the needle moves out of the initial position into the piercing position.

In some preferred embodiments, the switch cam engages with the cut-out disposed proximally of the lock window when the injection needle is in a position retracted into the distal end of the injection device, in the initial position and/or the end position.

In some preferred embodiments, the housing or an element secured to the housing has a projection pointing radially inwardly, which locates in an aperture disposed in the wall of the operating sleeve so far that the internal surface of the projection pointing radially inward is more or less flush with the internal surface of the operating sleeve pointing radially inward. This projection forms the distal boundary for the lock window. Due to the flush arrangement of the internal surfaces, the lock cam is able to slide off the internal surface of the projection onto the internal surface of the operating sleeve without any problem, as is the case when the needle is being moved out of the piercing position into the end position, for example. This being the case, the lock window is closed, i.e. its proximal boundary is in contact with the distal boundary so that the window width is zero.

In some preferred embodiments, the switch cam is coupled with a return spring, by which the switch cam and the injection needled connected to it in an axially fixed arrangement as well as the entire drive structure can be moved in the proximal direction. The switch cam is coupled with the return spring indirectly, for example via the holder for the product container and a function sleeve on which the return spring is supported, by or at its proximal end. The holder and the function sleeve are coupled with one another in an axially fixed arrangement so that they can act as a single part.

In some preferred embodiments, the return spring is a spiral compression spring which can be tensed when the function sleeve moves in the distal direction and relaxed when the function sleeve moves in the proximal direction. The return spring can be tensed by a driving spring. The driving spring may be used as a means of driving the needle forward out of the initial position into the piercing position and also for dispensing product. In some preferred embodiments, therefore, a single driving spring is sufficient.

In some preferred embodiments, an injection device in accordance with the present invention may have a lock element, which is connected to the switch cam via the drive structure in an axially fixed arrangement. The lock element is connected to the switch cam via the function sleeve and the holder for the product container. As a result, the lock element and switch cam are disposed at a fixedly defined axial distance from one another which remains unchanged during all the switching operations. The lock element may be moved into engagement with the cut-out disposed in the operating sleeve proximally of the lock window when the injection needle is in the piercing position. The lock element is moved into engagement with the cut-out when the piercing movement ends. As a result, the injection needle is blocked and can not be pulled back in the proximal direction out of the piercing position. The lock element may release a lock engagement with a plunger rod acting on the plunger as it engages so that the plunger rod is simultaneously driven by the driving spring for a dispensing movement.

In some embodiments, the movement of the lock element into engagement with the cut-out may also cause the return spring to be uncoupled from the driving spring once the driving spring has tensed the return spring during the piercing movement.

In some preferred embodiments, when the needle is in the piercing position and before the product has been fully dispensed, i.e. during the dispensing movement, the switch cam is engaged with the lock window and the lock element is engaged with the cut-out disposed in the operating sleeve. While the injection device is in this state, there is a short distance, e.g. 0.3 to 3 mm, between the proximal boundary of the lock window and the stop surface of the switch cam pointing in the proximal direction. At this point, the lock element is disposed with its stop surface pointing in the proximal direction in contact with the proximal boundary of the cut-out of the operating sleeve. The axial distance prevailing between the stop surface of the switch cam pointing in the proximal direction and the stop surface of the lock element pointing in the proximal direction is bigger, e.g. by a short distance, than the axial distance between the proximal boundary of the cut-out of the operating sleeve and the proximal boundary of the lock window. Due to this short distance, a haptic, tactile, or acoustic signal can be generated, indicating that product dispensing has terminated. In some preferred embodiments, the drive structure and hence the lock element and the switch cam can be moved by the return spring in the proximal direction by the amount of the short distance. As a result, the stop surface of the switch cam pointing in the proximal direction abruptly makes contact with the proximal boundary of the lock window, thereby generating the signal.

In some preferred embodiments, the lock element is able to unlatch or disconnect from the engagement with the cut-out when product dispensing has finished, as a result of which the return spring is able to relax by the short distance to generate the signal. In some preferred embodiments, the lock element is blocked to prevent it unlatching from the engagement with the cut-out by the external circumferential surface of the plunger rod moving past the lock element.

In some embodiments, the present invention comprises a method of retracting an injection needle extending from the distal end of an injection device into the distal end of the device, whereby the operating sleeve is moved out of the distal end of the injection device and a switch cam locating in a lock window is driven along by the operating sleeve as well. During the driving movement, the switch cam is moved out of the lock window. The switch cam fixedly connected to the injection needle is moved in the proximal direction so that the extracted injection needle is retracted into the distal end of the injection device. The method can be implemented entirely outside a subject's body, i.e. including all its method steps.

BRIEF DESCRIPTION OF THE DRAWINGS

FIGS. 1a and 1b are sectional diagrams of an embodiment of an injection device in accordance with the present invention, fitted with a cap, FIG. 1b showing a view rotated 90° about the longitudinal axis compared with FIG. 1a.

FIGS. 2a and 2b are sectional diagrams, showing the injection device of FIGS. 1a and 1b with the cap removed, FIG. 2b showing a view rotated 90° about the longitudinal axis compared with FIG. 2a.

FIGS. 3a and 3b are sectional diagrams showing the injection device of FIGS. 1a and 1b in an activated state, FIG. 3b showing a view rotated by 90° about the longitudinal axis compared with FIG. 3a.

FIGS. 4a and 4b are sectional diagrams showing the injection device in a triggered state, FIG. 4b showing a view rotated by 90° about the longitudinal axis compared with FIG. 4a.

FIGS. 5a and 5b are sectional diagrams showing the injection device in a piercing state, FIG. 5b showing a view rotated by 90° about the longitudinal axis compared with FIG. 5a.

FIGS. 7*a* and 7*b* are sectional diagrams showing the injection device in a state in which the injection device has emitted a clicking noise to signal the end of dispensing, FIG. 7*b* showing a view rotated 90° about the longitudinal axis compared with FIG. 7*a*.

FIG. 13 is a sectional diagram showing the signalling unit illustrated in FIG. 12.

FIG. 14 is another sectional diagram showing the signalling unit illustrated in FIG. 12.

DETAILED DESCRIPTION

Figure 3A:
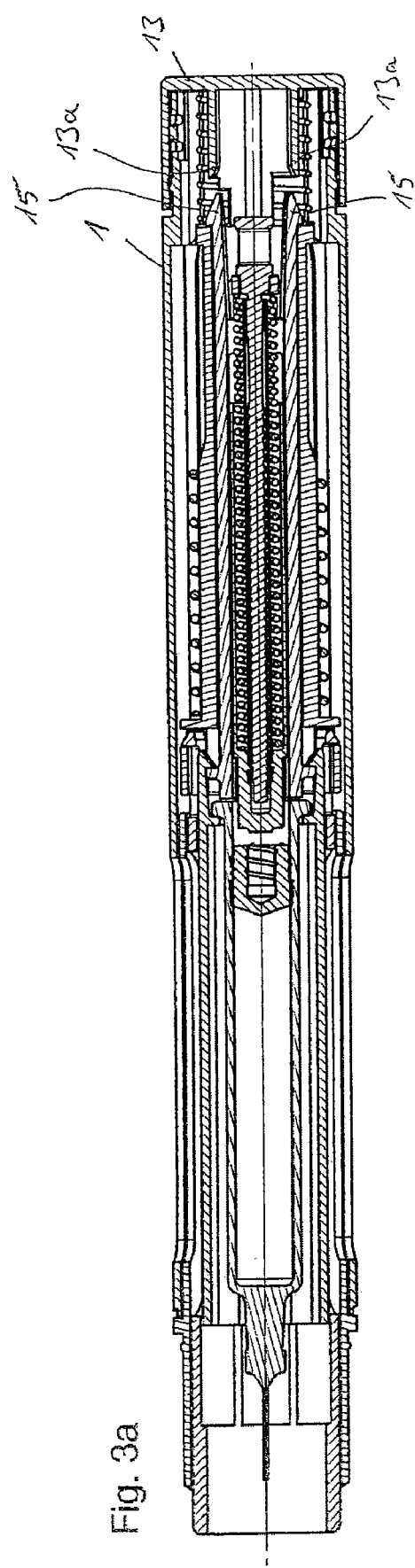

With regard to fastening, mounting, attaching or connecting components of the present invention, unless specifically described as otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making embodiments of the invention and/or components thereof may be selected from appropriate materials such as metal, metallic alloys, ceramics, plastics, etc. Unless stated otherwise, positional terms (e.g., up, down, front, rear, distal, proximal, etc.) are descriptive not limiting. Same reference numbers are used to denote same parts or components.

FIGS. 1*a* through 9*b* illustrate one preferred embodiment of an injection device in accordance with the present invention. Turning specifically to FIGS. 1*a* and 1*b*, the injection device comprises a housing 1, with a proximal (rear) housing part 1*a* and a distal (front) housing part 1*b* connected to the proximal housing part by a catch connection 1*c* so as to be axially fixed. The catch connection 1*c* comprises a window contained in or associated with the proximal housing part. An elastic tongue formed on the distal housing part 1*b* snaps into the window.

Accommodated in the housing 1 is a product container 2, on the distal end of which is an injection needle 4 for dispensing a liquid product contained in the product container 2. At the proximal end, the product container 2 has a displaceable plunger 3, the movement of which relative to the product container 2 and in the direction of the injection needle 4 causes product to be dispensed, which will also be referred to as a dispensing movement. The product container 2 is accommodated in the device so that it is able to move in the distal direction so that the injection needle 4 extends out beyond the distal end of the injection device. This may be thought of and/or referred to as a piercing movement. The product container 2 is connected to a holder 10 for the product container 2 in an axially fixed arrangement. The housing 1, i.e. its distal and proximal housing parts 1*a*, 1*b*, have a viewing window 12 through which the user of the injection device can see the product container 2. The holder 10 surrounds the product container 2 in a sleeve shape and either has a viewing window itself or, as in this example, is made from a transparent material to expose the view onto the container 2. The product container 2 is connected in an axially fixed arrangement by a clamp to a function sleeve 11 disposed proximally of it at the proximal end of the holder 10. At its proximal end, the product container 2 has a radially projecting collar, which is gripped by the clamp. At its distal end, the function sleeve 11 likewise has a radially projecting collar, which is also enclosed by the clamp. Accordingly, the product container 10, function sleeve 11 and holder 10 are connected to one another in an axially fixed arrangement so that they are able to move as a single part. This combination may be thought of and/or referred to herein as a drive structure.

The function sleeve 11 surrounds a plunger rod 5 which is able to act on the plunger 3 to dispense product. The plunger rod 5 has a sleeve-shaped part which surrounds a driving spring 6 and the driving spring 6 is supported distally on the plunger rod 5 and proximally on a switch sleeve 8, to a socket 8*a* disposed on it.

Adjoining the plunger rod 5 is a signalling unit, by which one or at least three or more haptic and/or acoustic signals can be generated for the piercing operation and/or the dispensing operation. The signalling unit comprises a catch rod 23 connected to the switch sleeve 8 and a locating sleeve 22 surrounding the catch rod 23 and connected, e.g. latched, in an axially fixed arrangement to the plunger rod 5. The locating sleeve 22 has a locating element 26 which engages in a groove 27 of the catch rod 23. At its proximal end, the catch rod 23 has a head 24, which is able to move in the proximal direction in a slide guide 25 formed by the activator element 13. The head engages by its distal end with a socket 8*a* disposed on the switch sleeve 8 and the engagement prevents the head 24 and hence the catch rod 23 from being able to move relative to the switch sleeve 8 in the distal direction. The way in which this arrangement operates will be explained later with reference to FIGS. 10 and 11, which provide a detailed illustration of the signalling unit illustrated in FIGS. 1 to 9. Alternatively, the signalling unit illustrated in FIGS. 10 and 11 may be replaced by a different signalling unit illustrated in FIGS. 12 to 14 and by yet another signalling unit illustrated in FIGS. 15 and 16. The injection device illustrated in FIGS. 1 to 9 does not have to undergo any major modification to this end.

When the injection device is in the initial state illustrated in FIGS. 1*a* and 1*b*, the driving spring 6 is tensed so that the needle 4 and the drive structure are advanced forward for a piercing movement and can push the plunger 3 to effect a dispensing movement. The function sleeve 11 has a lock element 16, on which a shoulder is disposed directed radially inwardly, which, in the initial state, co-operates with a shoulder directed radially outward on the distal end of the plunger rod 5 so that the plunger rod 5 is locked, thereby preventing a movement relative to the function sleeve 11. The lock element 16 is held in engagement with the plunger rod 5 by a surface of the switch sleeve 8 pointing radially inward. The lock element 16 is elastically connected to the function sleeve 11 by a resilient arm, and may be integral. The resilient arrangement may be designed so that the lock element 16 tends to move radially outward but this is prevented by the surface of the switch sleeve 8 pointing or extending radially inwardly.

At its proximal end, the function sleeve 11 has at least one snapper element 15, which snaps into the switch sleeve 8 in the initial state to prevent any movement of the function sleeve 11 and hence the drive structure. As a result, the pre-tensed spring 6 is not yet able to relax and the drive structure is not yet able to move in the distal direction.

At the proximal end of its housing 1, the injection device has an activator element 13, which is disposed so that it is axially stationary but can be rotated relative to the housing 1. The activator element 13 houses a return spring 21, which is supported distally on the proximal end of the switch sleeve 8 and proximally on the activator element 13. The purpose of the return spring 21 is to apply a force acting in the distal direction to the switch sleeve 8 and an operating sleeve 9 acting axially on the switch sleeve 8 so that the switch sleeve 8 and operating sleeve 9 are moved in the distal direction. The activator element 13 has an activator lock 14, which engages behind the snapper element 15 when the injection device is in the switching states illustrated in FIGS. 1a, 1b, 2a and 2b so that the snapper element 15 is blocked or locked and is not able to move out of engagement with the switch sleeve 8. This advantageously prevents the injection device from being inadvertently triggered. The activator lock can be moved out of engagement with the snapper element 15 by turning the activator element 13 by 90° relative to the housing 1, for example.

A return spring 7 acting in the longitudinal direction of the device is distally supported on the switch sleeve 8 and proximally supported on the function sleeve 11. As illustrated in this example, the return spring 7 surrounds the switch sleeve 8 and the function sleeve 11. The return spring 7 is proximally supported on a collar 11a disposed on the function sleeve 11, which extends radially outward through an aperture provided in the switch sleeve 8. In certain switch positions therefore, the return spring 7 is able to cause a relative movement between the switch sleeve 8 and function sleeve 11. The return spring 7 is a compression spring which is able to move the function sleeve 11 in the proximal direction relative to the switch sleeve 8. The return spring 7 is not pre-tensioned or is pre-tensioned with only a slight pre-tensioning force. For example, when the injection device is in the state illustrated in FIGS. 1a and 1b, the pre-tensioning force of the return spring 7 is lower than the pre-tensioning force of the driving spring 6.

Disposed distally of the switch sleeve 8 is the operating sleeve 9 which is able to move relative to the housing 1. The switch sleeve 8 and the operating sleeve 9 are mutually able to apply a pressing force to one another, e.g. latch or connect with one another, thereby pushing one another. To prevent the operating sleeve 9 blocking the view onto the product container 2, the operating sleeve 9 also has a window in the region of the window 12. Alternatively, the operating sleeve 9 may be made from a transparent material. When the return spring 21 is in the initial state, the operating sleeve 9 is pushed forward by the return spring 21 via the switch sleeve 8 distally beyond the distal end of the housing 1. The distal end of the operating sleeve 9 is used for positioning on an injection site of a patient.

The holder 10 has a switch cam 17, which engages in a cut-out 18 of the operating sleeve 9, which may be provided in the form of an aperture as illustrated in this example. The switch cam 17 is elastically connected, e.g. integrally, to the holder 10 by a resilient arm, for example. The switch cam 17 is biased so that it tends to engage in the cut-out 18 or move radially outward. The switch cam 17 projecting radially outward from the holder 10 has an oblique surface distally, which therefore also co-operates in pushing the switch cam 17 out of engagement with the cut-out 18. Proximally, the switch cam 17 also has a transversely extending stop surface, e.g. perpendicular to the longitudinal direction, which is able to make axial contact with the proximal boundary of the cut-out 18, as a result of which the switch cam 17 is not able to be moved out of the cut-out 18.

The operating sleeve 9 has an axial stop 19, with which the distal end of the holder 10 is able to make contact at the end of the piercing movement.

As illustrated in FIGS. 1a and 1b, the distal end of the injection device is fitted with a cap 32, which protects the interior of the injection device from dirt and keeps the needle 4 sterile. The cap 32 is removed prior to using the injection device so that the needle 4 and the operating sleeve 9 are exposed, as illustrated in FIGS. 2a and 2b. The state of the injection device illustrated in FIGS. 2a and 2b differs from the state illustrated in FIGS. 1a and 1b due to the fact that the cap 32 has been removed.

The force exerted on the injection device when the needle cap 32 is pulled off is transmitted via the holder 10 to the function sleeve 11, from where it is transmitted via the snapper 15 to the switch sleeve 8, which is supported on the operating sleeve 9. The operating sleeve 9 is in turn latched to the housing 1 via a projection 1d disposed on the distal housing part 1 so that the action of pulling the cap 32 off the injection device does not have any undesired effect on the mechanism.

In the switch state illustrated in FIGS. 2a and 2b, the operating sleeve 9 can not or can only very slightly be pushed into the distal end of the injection device because this sliding movement is transmitted via the switch sleeve 8 to the snapper 15 and the snapper 15 is prevented from moving in the proximal direction by the activator element 13.

Figure 3B:
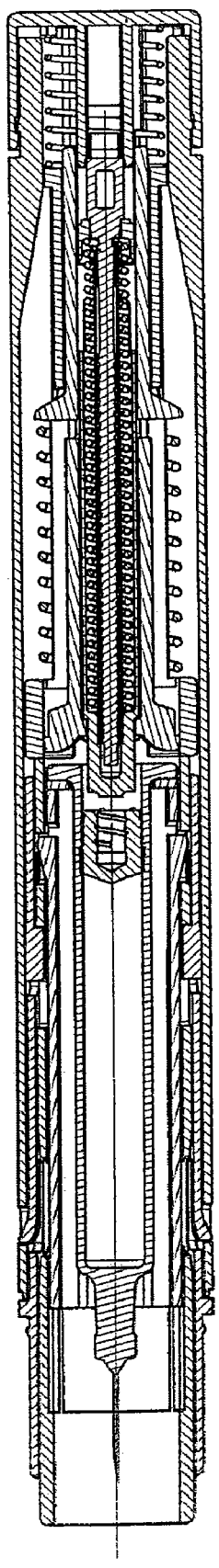

The injection device is illustrated in an activated state in FIGS. 3a and 3b, i.e. the injection device can be triggered. The injection device is activated or unlocked by a rotating movement of the activator element 13, e.g. by 90°. As this happens, the snapper elements 15 are released to permit a movement directed radially inwardly due to the fact that the activator lock 14 is moved out of engagement with the snapper elements 15, e.g. rotated. Consequently, there is space for the snapper elements 15 to be deflected inwardly. Like the snapper elements 15, the activator element 13 has an activator cam 13a, which is moved into a position axially flush with the snapper element 15 by the rotating movement of the activator element 13. Proximally, the snapper elements 15 and, distally, the activator cam 13a disposed proximally of it have a contour which can deflect the snapper element 15 radially inwardly as the snapper element 15 moves into engagement with the activator cam 13. In this example, the contours are two oblique planes extending down towards one another.

To trigger the injection device, the user of the device places it with the distal end on the injection site, which typically will have been disinfected beforehand. As a result, the operating sleeve 9 is moved in the proximal direction relative to the housing 1, until the distal end of the operating sleeve 9 is more or less flush with the distal end of the distal housing part 1b. Due to the movement of the operating sleeve 9, the switch sleeve 8 is also slaved in the proximal direction, causing the snappers 15 to be pushed radially inwardly by the activator cam 13a out of engagement with the switch sleeve 8. As the operating sleeve 9 moves in the distal direction, the elements of the drive structure are also moved in the proximal direction, as long as the snapper elements 15 are snapped into the switch sleeve 8. Since the plunger rod 5 is in a locked engagement with the function sleeve 11, the plunger rod 5 is also moved in the proximal direction. The signalling unit accommodated in the plunger rod 5 is likewise moved in the proximal direction. The head 24 disposed proximally on the catch rod 23 is able to slide along the guide 25 formed by the activator element 13.

Since no relative movement can yet take place between the activator sleeve 11 and the switch sleeve 8 during this movement, neither the return spring 7 nor the driving spring 6 are tensed or relaxed.

The force which the user of the device must apply to the housing 1 to push the operating sleeve 9 in the proximal direction is determined by the force of the return spring 21 against which the switch sleeve 8 and the operating sleeve 9 are moved. In some preferred embodiments, the spring 21 is a compression spring and is made from a plastic material. Alternatively, it would naturally also be possible to use springs made from spring steel material or some other spring material. The activator element 13 is axially secured to the housing 1 by, e.g., a snap ring connection to the housing. If the operating sleeve 9 is not pushed far enough toward the injection site and the snapper elements 15 are not released from the engagement with the switch sleeve 8, the trigger mechanism, e.g. the switch sleeve 8 and the operating sleeve 9, are re-set by the return spring 21 when the injection device is moved away from the injection site.

As may be seen from FIG. 4b, a lock window 20 is formed due to the movement of the operating sleeve 9 in the proximal direction, which is bounded distally by the housing 1 and/or the projection 1d, and proximally by the operating sleeve 9. Since no relative movement can yet take place between the drive structure and the operating sleeve 9 as the operating sleeve 9 is moving in the proximal direction, the switch cam 17 remains in the cut-out 18.

Once the snappers 15 have been released from the engagement with the switch sleeve 8, the driving spring 6 is able to relax to a certain extent, as a result of which the drive structure is pushed in the distal direction. This being the case, the injection needle 4 moves beyond the distal end of the injection device. Since the function sleeve 11 moves relative to the switch sleeve 8 during this piercing movement, the return spring 7 is compressed, i.e. tensed. The spring force of the driving spring 6 is stronger than the spring force of the return spring 7 during the entire piercing operation, i.e. including at the start and at the end of the piecing operation. An advantage of this is that the piercing force is reduced, for example, which prevents the injection device from damage.

Figure 5A:
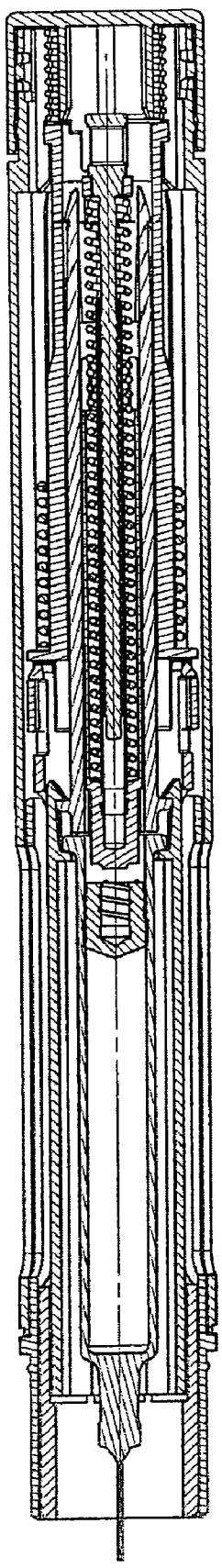
Figure 5B:
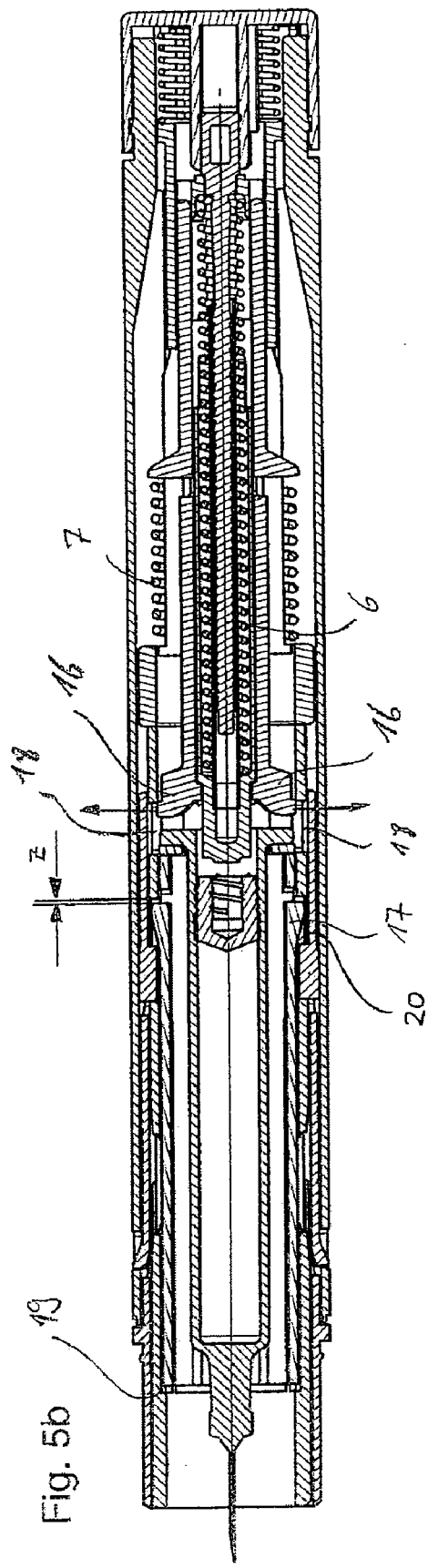

As may be seen from FIGS. 5a and 5b illustrating the situation at the end of the piercing operation, the lock element 16 engages in the cut-out 18 by a radially outward movement, as indicated by the arrows in FIG. 5b. The lock element 16 has a projection directed radially outward. The lock element 16 fulfils a dual function. As the lock element 16 latches in the cut-out 18, the lock element 16 is simultaneously released from the plunger rod 5 by the movement directed radially outward, releasing the latter for a dispensing movement. Conversely, the movement of the drive structure in the axial direction, i.e. the proximal direction, is blocked. As a result of this operation, the driving spring 6 is uncoupled from the return spring 7, i.e. the driving spring 6 has no effect on the tensioning of the return spring 7 in this state. A dispensing movement then follows, during which a clicking noise is emitted at constant times by the signalling unit, which is perceptible to the user of the device.

No additional force due to the piercing operation can be felt by the user of the device. This is absorbed by the snapping action between the operating sleeve 9 and the switch sleeve 8 and is not transmitted to the housing. The force for the piercing operation is directed via the function sleeve 11 to the collar of the product container 2. The piercing operation is therefore forcibly controlled because the function sleeve 11 drives the product container 2 forwards until the end of dispensing and the plunger rod 5 is not able to dispense until the lock elements 16 have located in the cut-outs 18. The piercing movement is stopped by the stop 19 on the operating sleeve 9.

During the piercing movement, the switch cam 17 is forced out of the engagement with the cut-out 18 due to its distal design of the distal boundary of the cut-out 18 of the operating sleeve 9 and pushed in the distal direction so that it latches in the lock window 20, as illustrated in FIGS. 5a and 5b. The lock element 16 latched in the cut-out 18 in contact with the proximal boundary of the cut-out 18. Since the lock element 16 and the switch cam 17 are disposed at a defined distance from one another due to their axially fixed arrangement, there is a short distance between the proximal end of the switch cam and the distal end of the lock window 20 when the lock element 16 is engaged by the cut-out, which in this instance is 0.5 to 1 mm, for example. As explained in more detail below, this distance is used to produce a haptic or acoustic signal which is intended to indicate that the product has been fully dispensed. The short distance z results from the difference between the distance existing between the stop surface of the switch cam 17 pointing in the proximal direction and the stop surface pointing in the proximal direction, and the distance of the proximal boundaries of the cut-out 18 and the lock window 20.

Figure 6A:
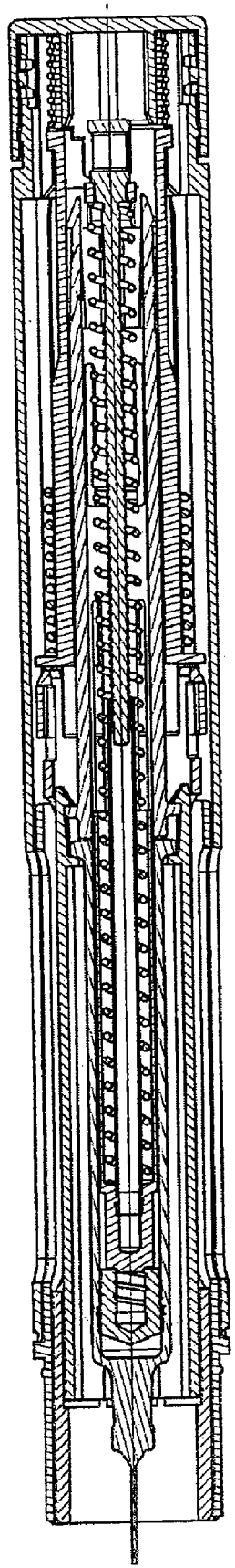
FIGS. 6*a* and 6*b* are sectional diagrams showing the injection device in a dispensed state, FIG. 6*b* showing a view rotated 90° about the longitudinal axis compared with FIG. 6*a*.
Figure 6B:
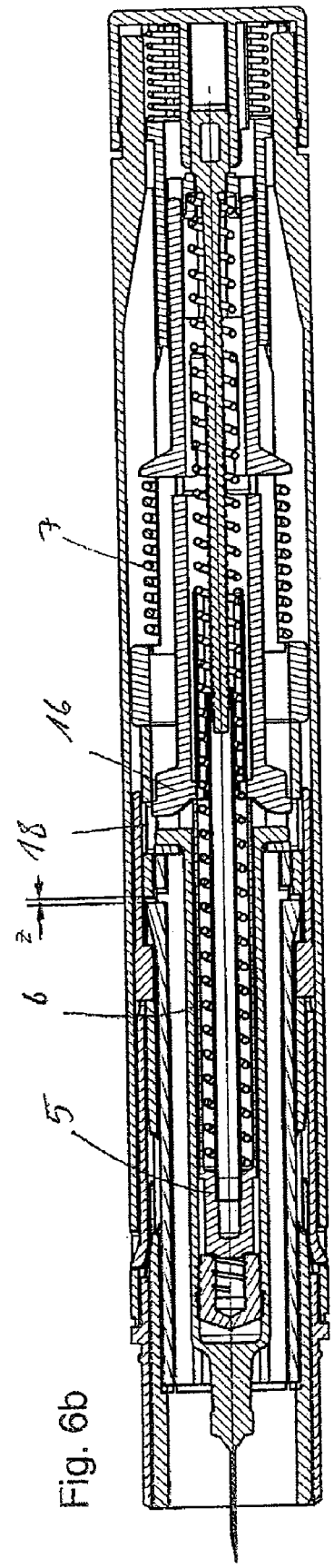
Figure 8A:
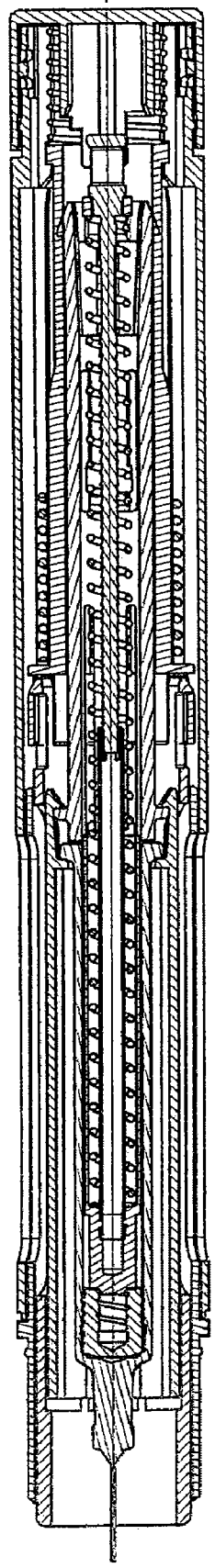
FIGS. 8*a* and 8*b* are sectional diagrams showing the injection device in a situation in which retraction of the injection needle has been activated, FIG. 8*b* showing a view rotated 90° about the longitudinal axis compared with FIG. 8*a*.
Figure 8B:
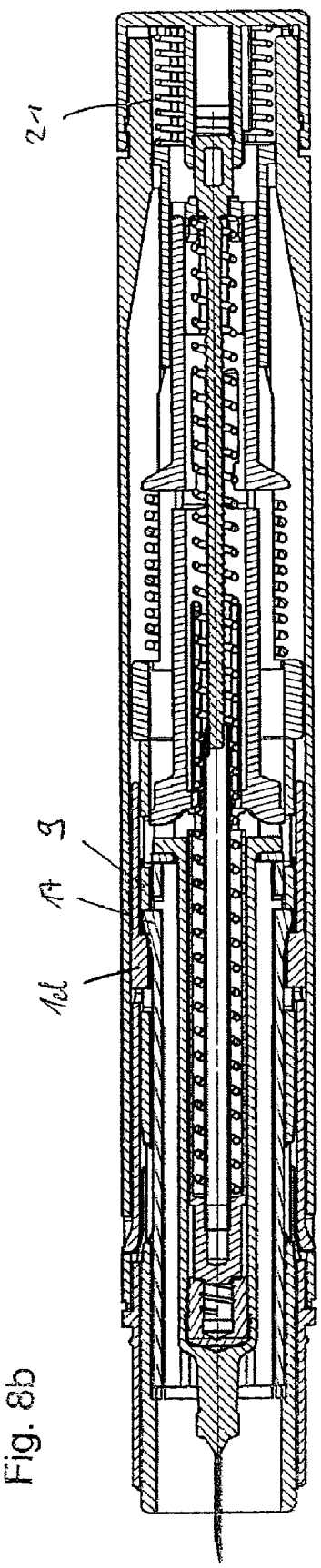

FIGS. 6a and 6b illustrate the injection device in a state in which a product has been dispensed. During dispensing of the product, the external circumferential surface of the sleeve-shaped part of the plunger rod 5 pushes the lock element 16 into the cut-out 18, as a result of which the lock element 16 is locked to prevent it from unlatching from the cut-out 18 while product is being dispensed. The plunger rod 5 may have a cut-out or may be of such a length that when the product has been dispensed, the locking action of the lock element 16 by the external circumferential surface of the plunger rod 5 disappears so that the lock element 16 is able to unlatch from the cut-out 18 as illustrated in FIG. 6b. The unlatching action may be caused by an elastically biased arrangement of the lock element 16 or due to the geometry of the lock element 16, which causes the lock element 16 to be pushed out of the cut-out 18.

At the end of dispensing the product, the driving spring 6 has further relaxed, while the tensioning of the tensed return spring 7 remains constant. The spring force of the driving spring 6 is now weaker than the spring force of the tensed return spring 7. When the engagement of the lock element 16 with the cut-out 18 is released, the return spring 7 and driving spring 6 are coupled with one another again. As illustrated in FIGS. 7a and 7b, this coupling causes the short distance z (see FIGS. 5b and 6b) to disappear because the drive structure, and/or the associated switch cam 17, is moved abruptly onto the distal end of the lock window 20. As the switch cam 17 makes contact, a haptic and/or acoustic signal is generated. This movement by the short distance z does not yet cause the needle 4 to be completely retracted from the patient, however. The patient or user of the device can now wait any time until the needle has been completely pulled out of the patient because he or she can selectively initiate the automatic retraction of the needle of the device.

A complete movement of the needle into the distal end of the housing 1 is still not possible because, as may be seen from FIG. 7b, the switch cam 17 is engaged with the lock window 20 and is thus preventing the spring 7 from relaxing.

To release retraction of the needle 4, the user of the device merely has to remove the latter from the injection site. As a result, the return spring 21 is able to move the operating sleeve 9 in the distal direction via the switch sleeve 8. As this happens, the drive structure is stationary relative to the operating sleeve 9 so that the switch cam 17 is pushed radially inward out of the lock window 20, due to its distal shape, driven by the spring 21 connected to the operating sleeve 9 by the projection 1d. As soon as the switch cam 17 is pushed inward, the needle 4 is free to retract. Also as a result of the releasing action, the return spring 7 is released for a retracting movement. Due to the stronger spring force of the pre-tensed return spring 7, the entire drive structure is pushed in the proximal direction. As a result, the spring 6 is tensed again and the spring force of the return spring 7 is stronger than the spring force of the driving spring 6 during the entire retraction operation, i.e. including up to the end of the retracting movement.

Figure 9A:
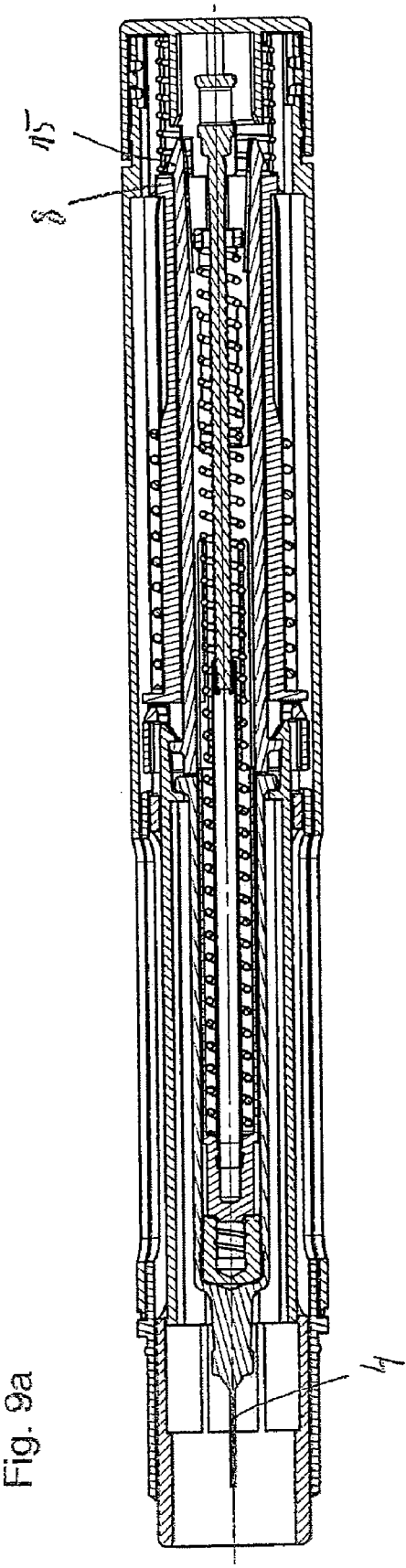
FIGS. 9*a* and 9*b* are sectional diagrams showing the injection device in a final state, FIG. 9*b* showing a view rotated 90° about the longitudinal axis compared with FIG. 9*a*.
Figure 9B:
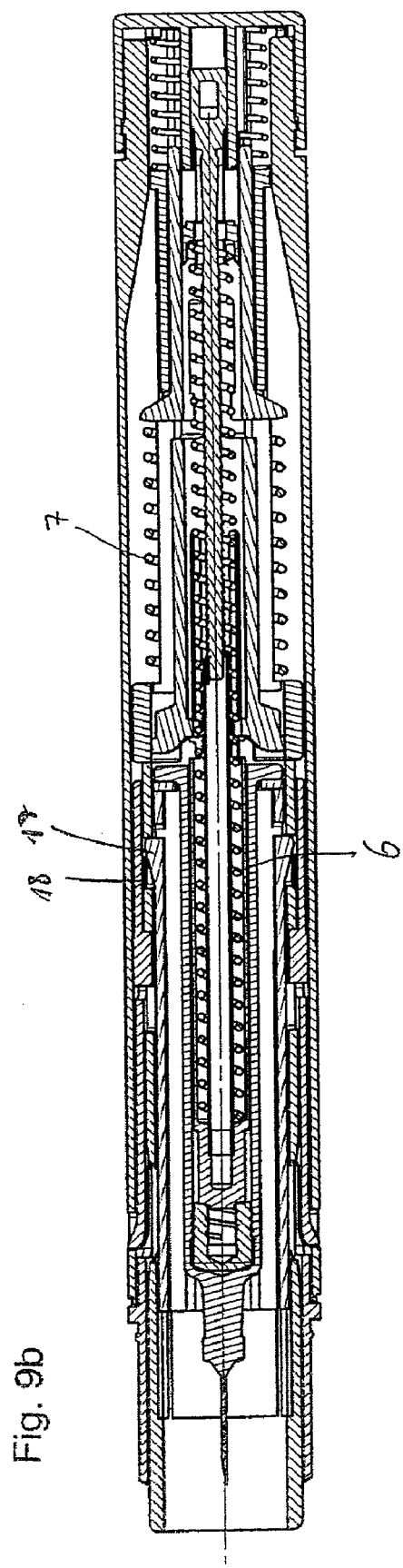

FIGS. 9a and 9b illustrate the injection device in a final state. In this state, the injection device has again the same dimensions it had at the start. The cap 32 can be fitted again and the injection device disposed of. In the end position, the needle has been completely retracted into the distal end of the device. The snapper element 15 is latched to the switch sleeve 8 again, as at the start. However, it is not possible to trigger the injection device again because a pretensioned driving spring 6 would be necessary to do this, as illustrated in FIG. 1a, for example.

Figures 10, 11:
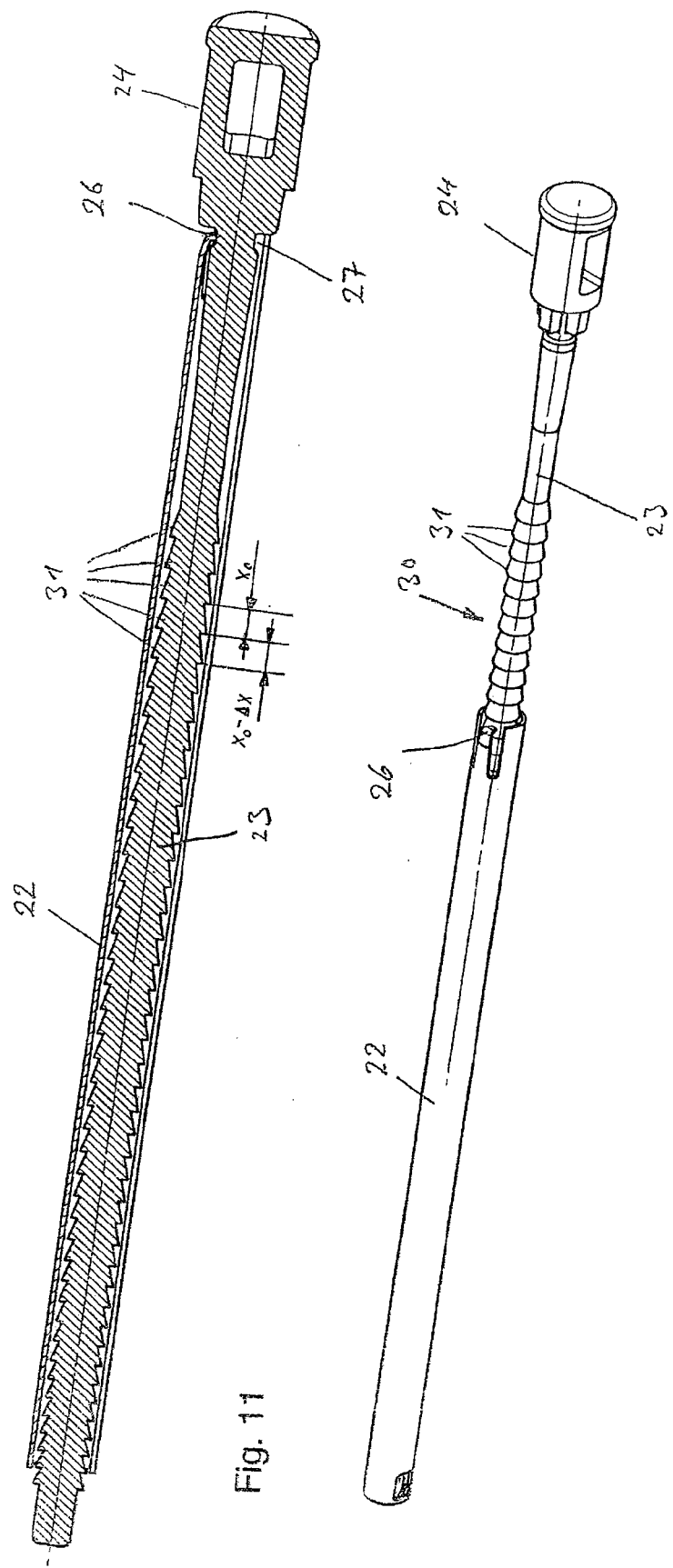
FIG. 10 is a sectional diagram showing the signalling unit illustrated in FIGS. 1 to 9.
FIG. 11 is a perspective view of the signalling unit illustrated in FIG. 10.

FIGS. 10 and 11 provide detailed illustrations of the signalling unit illustrated in FIGS. 1 to 9. The catch rod 23 has a catch 30 comprising a plurality of catch elements 31, disposed along the longitudinal direction at distances which decrease in steps. These distances become smaller on the basis of the easing spring force. The catch rod is connected to the switch sleeve 8 (FIG. 1 for example) by its proximal end, e.g. by its head, so as to be axially fixed in at least one direction. The catch rod 23 is surrounded by a catch sleeve 22, which is connected by the distal end to the driving spring 6 and/or to the distal end region of the plunger rod 5. The locating sleeve has a locating element 26 which engages in an annular groove 27. The locating element 26 engages in the groove 27 in the initial position. During the driving movement which takes place until piercing, i.e. during the piercing movement, the locating element unlatches from the groove 27 and moves across a first portion of the catch rod as far as the start of the plurality of catch elements 31. The first part has no other catch element but is of a cylindrical shape or tapers so that no signals are emitted during the piercing movement. In principle, embodiments are possible where this might be an advantage. The length of the first portion is dimensioned so that the locating element 26 has moved completely past the first portion once the piercing movement has ended. At the start of the dispensing movement, the rod 23 and sleeve 22 are pulled even further apart so that the locating element 26 moves across the second portion, i.e. the portion with the catch element 31, thereby moving past the respective catch elements 31. On moving past each of the catch elements, a short clicking signal is emitted. The time intervals from one clicking signal to the next one are constant, although the easing spring force reduces the speed of the locating element 26 as the distance traveled increases. The distances from one catch element to the next decrease with the spring travel. This makes allowance for the changing speed.

On the side radially opposite that on which the locating element 26 is disposed, another locating element 26 may be provided, for example. In some embodiments, another locating element 26, as illustrated, is not provided, but only a support formed by the sleeve wall which acts as a thrust bearing.

Figure 12:
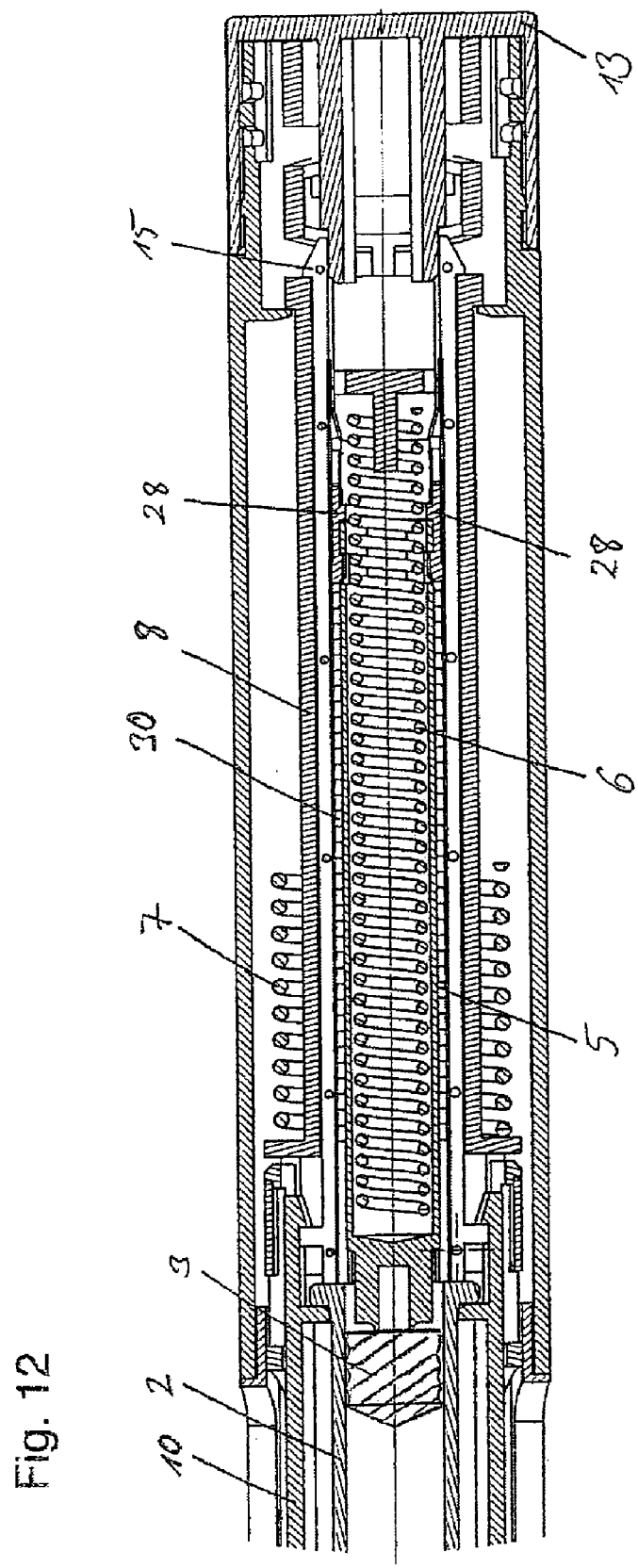
FIG. 12 illustrates another embodiment of an injection device in accordance with the present invention with a different embodiment of a signalling unit.

FIGS. 12 to 14 illustrate an alternative embodiment of the signalling unit for the embodiment of the injection device illustrated in FIGS. 1 to 9. The catch 30 is disposed in a groove 29, namely against its flank. The catch elements 31 project out from the groove flank in the circumferential direction. Disposed in the groove 29 is an axially displaceable carriage 28 which is coupled with the plunger rod 5 in an axially fixed arrangement. During the dispensing movement, the carriage 28 is taken along by the plunger rod 5, as a result of which the locating element 26 resiliently arranged on the carriage 28 travels across the individual catch elements 31 of the catch 30. Here too, the catch elements 31 are respectively disposed at distances apart from one another which permit an emission of signals at constant times making allowance for the changing force of the driving spring. The distance of the sawteeth is selected so that the individual clicks occur at identical time intervals even though the carriage 28 together with the plunger rod 5 has a slower dispensing speed at the end of dispensing than at the start.

Figure 16:
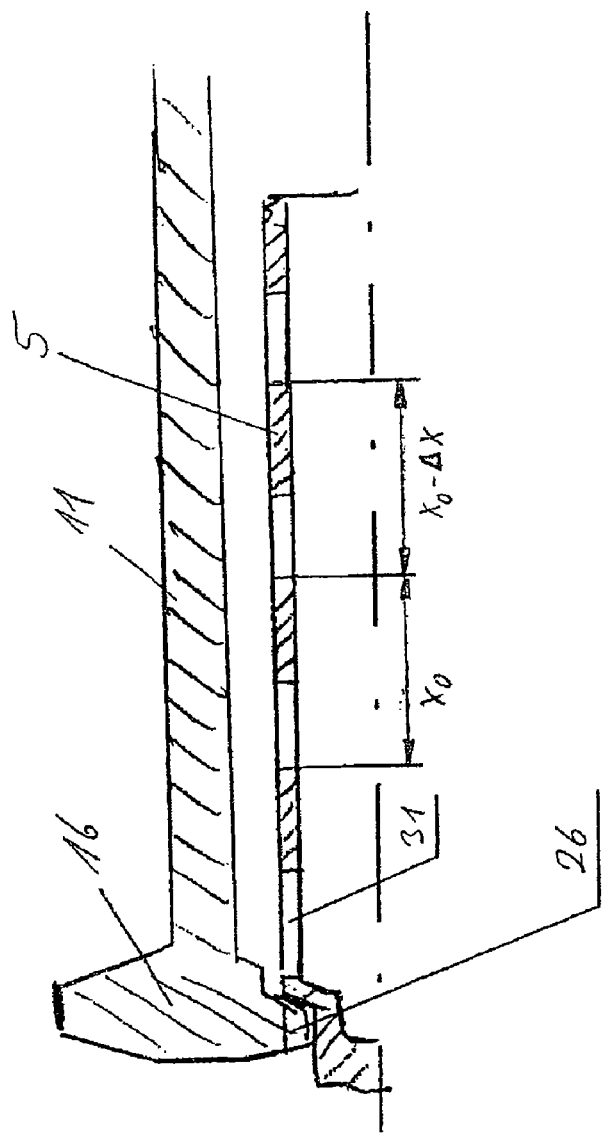
FIGS. 15 and 16 illustrate another embodiment of a signalling unit in accordance with the present invention.
Figure 15:
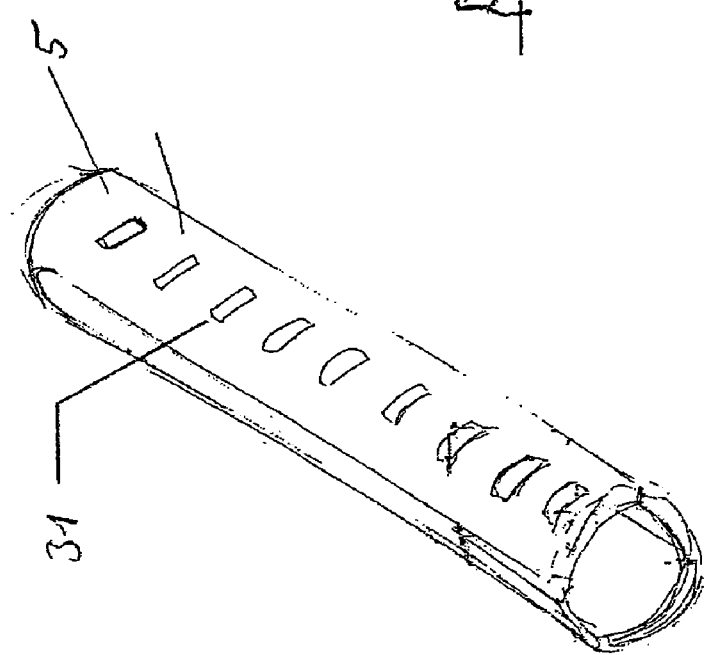

FIGS. 15 and 16 illustrate another embodiment of the signalling unit in which the catch 30 is provided in the form of cut-outs, e.g. windows, which are also disposed on the plunger rod 5 at varying distances. The locating element 26 is resiliently mounted on the function sleeve 11. During the dispensing movement, the plunger rod 5 and hence the perforated catch 30 is moved along past the locating element 26 which locates respectively in each perforated catch 31 and thus generates the signal. An advantage of this embodiment is that the locating element 26 is formed by the lock element 16, which means that this embodiment requires a small number of parts.

Embodiments of the present invention, including preferred embodiments, have been presented for the purpose of illustration and description. They are not intended to be exhaustive or to limit the invention to the precise forms and steps disclosed. The embodiments were chosen and described to illustrate the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:
1. An injection device comprising:
 a housing,
 an actuating sleeve carried by the injection device to be movable relative to the housing and which can be placed at a point of injection in a position of insertion,
 an injection needle extendable from the end of the injection device when the injection device is in the position of insertion and moveable into the interior of the injection device, and
 an actuating cam arranged in an axially fixed manner relative to the injection needle and engageable in a locking recess when the injection device is in the position of insertion to prevent the injection needle from being moved into the interior of the injection device, said actuation cam being releasable from engagement with the locking recess by the actuating sleeve, thereby releasing the injection needle for movement into the injection device.

2. An automatic injection device comprising:
a) a housing,
b) an operating sleeve that can be placed on an injection site of a patient and is configured to slide proximally relative to the housing to trigger a piercing movement of an injection needle, wherein the injection needle projects beyond a distal end of the injection device in a piercing position and can be retracted into the interior of the injection device; and
c) a switch cam disposed in an axially fixed arrangement with respect to the injection needle and engageable in a lock window in the piercing position to prevent the injection needle from moving into the interior of the injection device, wherein the switch cam is moveable out of engagement with the lock window by the operating sleeve so that the injection needle is released for the retracting movement.

3. The injection device as claimed in claim 2, wherein the housing or an element secured to the housing bounds the lock window distally and the operating sleeve bounds the lock window proximally.

4. The injection device as claimed in claim 2, wherein the width of the lock window in the longitudinal direction of the injection device is variable so that the switch cam is able to move into or out of engagement with the lock window depending on the width of the lock window.

5. The injection device as claimed in claim 2, wherein the switch cam has a stop surface extending in the proximal direction which is able to co-operate with the operating sleeve so that the switch cam can also be driven by the operating sleeve as the operating sleeve moves in the distal direction when the switch cam is disposed in the lock window.

6. The injection device as claimed in claim 3, wherein a distal portion of the switch cam is shaped so that it can be moved out of engagement with the lock window by the housing or the element secured to the housing and it can be moved by the operating sleeve out of engagement with a cut-out formed by the operating sleeve.

7. The injection device as claimed in claim 2, further comprising an elastic element which can be tensed due to a movement of the operating sleeve in the proximal direction and by which the operating sleeve is driven to move in the distal direction.

8. The injection device as claimed in claim 2, wherein the switch cam engages with a cut-out in the operating sleeve proximally of the lock window when the injection needle is retracted into the interior of the injection device.

9. The injection device as claimed in claim 8, wherein the retracted position is an initial position or an end position.

10. The injection device as claimed in claim 2, wherein the housing or an element secured to the housing has a projection extending radially inwardly sufficiently far through an aperture in the operating sleeve that an internal surface of the projection is approximately flush with the internal surface of the operating sleeve.

11. The injection device as claimed in claim 2, wherein the switch cam is resiliently disposed on a part of a drive structure of the injections device.

12. The injection device as claimed in claim 11, wherein the drive structure comprises a holder for a product container and the switch cam is on the holder.

13. The injection device as claimed in claim 2, wherein the switch cam is coupled with a return spring, by which return spring the switch cam and the injection needle can be moved in the proximal direction.

14. The injection device as claimed in claim 2, further comprising a lock element connected to the switch cam via a drive structure in an axially fixed arrangement and moveable into engagement with a cut-out disposed on the operating sleeve proximally of the lock window when the injection needle is in the piercing position.

15. The injection device as claimed in claim 14, wherein the switch cam engages with the lock window and the lock element engages with the cut-out when the needle is in the piercing position.

16. The injection device as claimed in claim 15, wherein there is a short distance between the proximal boundary of the lock window and a stop surface of the switch cam in the proximal direction, and a stop surface of the lock element is in contact with the proximal boundary of the cut-out of the operating sleeve.

17. The injection device as claimed in claim 16, wherein the short distance is between approximately 0.3 to 3 mm.

18. The injection device as claimed in claim 16, wherein the drive structure is moveable by a return spring by a distance corresponding to the short distance, thereby generating at least one of a haptic or acoustic signal.

19. A method of retracting an injection needle extending from a distal end of an injection device into an interior of the injection device, the method comprising the steps of:
moving an operating sleeve out of the distal end of the injection device, whereby a switch cam located in a lock window is moved along by the operating sleeve,
moving the switch cam out of the lock window during a driving movement, whereby the injection needle is retracted into the interior of the injection device under the force of an energy storing element.

* * * * *